(12) United States Patent
Brusatore

(10) Patent No.: US 10,070,594 B2
(45) Date of Patent: Sep. 11, 2018

(54) METHOD AND APPARATUS FOR AUTOMATED VERTICAL HORTICULTURE AND AGRICULTURE

(71) Applicant: AFFINOR GROWERS INC., Vancouver (CA)

(72) Inventor: Nicholas G. Brusatore, Port Coquitlam (CA)

(73) Assignee: Affinor Growers Inc., Vancouver (CA)

( * ) Notice: Subject to any disclaimer, the term of this patent is extended or adjusted under 35 U.S.C. 154(b) by 199 days.

(21) Appl. No.: 15/120,011

(22) PCT Filed: Feb. 19, 2015

(86) PCT No.: PCT/CA2015/050127
§ 371 (c)(1),
(2) Date: Aug. 18, 2016

(87) PCT Pub. No.: WO2015/123776
PCT Pub. Date: Aug. 27, 2015

(65) Prior Publication Data
US 2017/0055460 A1    Mar. 2, 2017

Related U.S. Application Data

(60) Provisional application No. 61/942,500, filed on Feb. 20, 2014.

(51) Int. Cl.
*A01G 7/00* (2006.01)
*A01G 9/12* (2006.01)
(Continued)

(52) U.S. Cl.
CPC ............... *A01G 9/12* (2013.01); *A01G 7/02* (2013.01); *A01G 7/045* (2013.01); *A01G 9/20* (2013.01);
(Continued)

(58) Field of Classification Search
CPC . A01G 7/02; A01G 7/045; A01G 9/12; A01G 9/20; A01G 9/023; A01G 31/02;
(Continued)

(56) References Cited

U.S. PATENT DOCUMENTS

| 1,500,917 A | 7/1924 | Bell |
| 3,254,447 A | 6/1966 | Ruthner |

(Continued)

FOREIGN PATENT DOCUMENTS

| CA | 2343254 | 7/2001 |
| CA | 2396317 | 11/2002 |

(Continued)

OTHER PUBLICATIONS

PCT International Search Report and the Written Opinion in International Application No. PCT/CA2015/050127 dated May 7, 2015.

*Primary Examiner* — Richard G Davis
(74) *Attorney, Agent, or Firm* — Bruce M. Green; Oyen Wiggs Green & Mutala LLP

(57) ABSTRACT

A method and apparatus for continuous automated growing of plants utilizes a vertical array of plant supporting arms extending radially from a central axis. Each arm has a plurality of pot receptacles which receive the plant seedling and liquid nutrients and water. The potting arms are rotated beneath grow lamps and pollinating arms. The frequency of feeding is increased as the plants grow. $CO^2$ enriched air may also be provided. Once the plants are ready to harvest, they are manually exchanged for new seedlings and packaged.

9 Claims, 6 Drawing Sheets

(51) Int. Cl.
| | |
|---|---|
| *A01G 31/06* | (2006.01) |
| *A01G 31/04* | (2006.01) |
| *A01G 7/02* | (2006.01) |
| *A01G 7/04* | (2006.01) |
| *A01G 9/20* | (2006.01) |
| *A01G 27/00* | (2006.01) |
| *A01H 1/02* | (2006.01) |

(52) U.S. Cl.
CPC ............. *A01G 27/00* (2013.01); *A01G 31/04* (2013.01); *A01G 31/06* (2013.01); *A01H 1/025* (2013.01); *Y02P 60/216* (2015.11)

(58) Field of Classification Search
CPC ...... A01G 31/04; A01G 31/047; A01G 31/06; Y02P 60/216; Y02P 60/146
See application file for complete search history.

(56) References Cited

U.S. PATENT DOCUMENTS

| | | | |
|---|---|---|---|
| 3,339,308 A | 9/1967 | Clare | |
| 3,529,379 A | 9/1970 | Ware | |
| 3,667,157 A | 6/1972 | Longhini | |
| 3,747,268 A | 7/1973 | Linder | |
| 3,772,827 A | 11/1973 | Ware | |
| 3,824,736 A | 7/1974 | Davis | |
| 3,882,634 A | 5/1975 | Dedolph | |
| 3,909,978 A | 10/1975 | Fleming | |
| 3,973,353 A | 8/1976 | Dedolph | |
| 4,085,544 A | 4/1978 | Blake | |
| 4,255,897 A | 3/1981 | Ruthner | |
| 4,258,501 A * | 3/1981 | Brown | A01G 31/047 47/16 |
| 4,356,664 A | 11/1982 | Ruthner | |
| 5,165,364 A | 11/1992 | Horkey | |
| 5,372,474 A | 12/1994 | Miller | |
| 5,515,648 A | 5/1996 | Sparkes | |
| 5,584,141 A | 12/1996 | Johnson | |
| 5,617,673 A | 4/1997 | Takashima | |
| 5,862,628 A | 1/1999 | Takashima | |
| 6,378,246 B1 | 4/2002 | DeFoor | |
| 6,394,030 B1 | 5/2002 | Geiger et al. | |
| 6,557,491 B1 | 5/2003 | Weiser et al. | |
| 6,604,321 B2 | 8/2003 | Marchildon | |
| 6,840,007 B2 | 1/2005 | Leduc et al. | |
| 7,143,544 B2 | 12/2006 | Roy | |
| 7,168,206 B2 | 1/2007 | Agius | |
| 7,181,886 B2 | 2/2007 | Bourgoin et al. | |
| 7,188,451 B2 | 3/2007 | Marchildon | |
| 7,401,437 B2 | 7/2008 | Dumont | |
| 7,415,796 B2 | 8/2008 | Brusatore | |
| 7,488,098 B2 | 2/2009 | Dumont | |
| 7,533,493 B2 | 5/2009 | Brusatore | |
| 7,559,173 B2 | 7/2009 | Brusatore | |
| 7,818,917 B2 | 10/2010 | Brusatore | |
| 7,984,586 B2 | 7/2011 | Brusatore | |
| 8,234,814 B2 | 8/2012 | Kertz | |
| 8,418,403 B1 * | 4/2013 | Nuttman | A01G 9/024 47/82 |
| 9,374,952 B1 * | 6/2016 | Cross | A01G 31/02 |
| 2002/0144461 A1 | 10/2002 | Marchildon | |
| 2004/0111965 A1 | 6/2004 | Agius | |
| 2004/0163308 A1 | 8/2004 | Uchiyama | |
| 2005/0011119 A1 | 1/2005 | Bourgoin et al. | |
| 2005/0039396 A1 | 2/2005 | Marchildon | |
| 2005/0039397 A1 | 2/2005 | Roy | |
| 2005/0055878 A1 | 3/2005 | Dumont | |
| 2005/0257424 A1 | 11/2005 | Bissonnette et al. | |
| 2006/0150481 A1 | 7/2006 | Hung et al. | |
| 2006/0196118 A1 | 9/2006 | Brusatore | |
| 2006/0230674 A1 | 10/2006 | Marchildon | |
| 2007/0141912 A1 | 6/2007 | Dumont | |
| 2007/0251145 A1 | 11/2007 | Brusatore | |
| 2007/0271842 A1 | 11/2007 | Bissonnette et al. | |
| 2008/0110088 A1 | 5/2008 | Brusatore | |
| 2008/0222949 A1 | 9/2008 | Bissonnette et al. | |
| 2010/0115837 A1 | 5/2010 | Van Der Poel et al. | |
| 2010/0146854 A1 * | 6/2010 | Cannon | A01G 9/023 47/82 |
| 2010/0236147 A1 | 9/2010 | Brusatore | |
| 2011/0192082 A1 | 8/2011 | Uchiyama | |
| 2013/0145690 A1 * | 6/2013 | Cannon | A01G 9/023 47/66.7 |
| 2014/0196363 A1 * | 7/2014 | Chung | A01G 31/047 47/1.7 |
| 2015/0223418 A1 * | 8/2015 | Collins | A01G 31/02 47/62 R |
| 2015/0334930 A1 * | 11/2015 | Stoltzfus | A01G 31/06 47/62 A |

FOREIGN PATENT DOCUMENTS

| | | |
|---|---|---|
| CA | 2412073 | 5/2004 |
| CA | 2503705 | 6/2004 |
| CA | 2431523 | 12/2004 |
| CA | 2536116 | 2/2005 |
| FR | 2240684 | 3/1975 |
| FR | 2345912 | 10/1977 |
| FR | 2680074 | 2/1993 |
| GB | 2026831 | 2/1980 |
| GB | 2269304 | 2/1994 |
| JP | 4229111 | 8/1992 |
| JP | 201128571 | 5/2001 |
| RU | 2034448 | 5/1992 |
| SU | 650557 | 3/1979 |
| SU | 914004 | 3/1982 |
| SU | 1722301 | 3/1992 |
| WO | 2006096650 | 9/2006 |
| WO | 2008156538 | 12/2008 |
| WO | 2010029993 | 3/2010 |
| WO | 2010110844 | 9/2010 |
| WO | 2011067548 | 9/2011 |

\* cited by examiner

US 10,070,594 B2

METHOD AND APPARATUS FOR AUTOMATED VERTICAL HORTICULTURE AND AGRICULTURE

CROSS REFERENCE TO RELATED APPLICATION

The present application claims the benefits, under 35 U.S.C.§ 119(e), of U.S. Provisional Application Ser. No. 61/942,500 filed Feb. 20, 2014 entitled "Method and Apparatus for Automated Vertical Horticulture and Agriculture" which is incorporated herein by this reference.

TECHNICAL FIELD

The invention relates to the fields of horticulture, hydroponics and agriculture and particularly apparatus and methods for automated commercial growth and production of plants in controlled environments.

BACKGROUND

Traditionally the commercial horticultural and agricultural growth of plants has been carried out in nurseries and greenhouses, where the plants are arranged horizontally and are stationary. More efficient methods have more recently been developed, some of which are referred to as 'vertical farming' The present inventor, for example, in U.S. Pat. Nos. 7,415,796, 7,533,494, 7,559,173, 7,818,917 and 7,984,586 disclosed methods of growing plants using a rotating vertical carousel of rotating spheres, each having a central light source around which rows of plants are rotated, to thereby increase the productivity of plant growth in a given area. However harvesting of mature plants from such systems can be complicated and time consuming.

The foregoing examples of the related art and limitations related thereto are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

The present invention provides a method and apparatus for continuous automated growing of plants. A vertical array of plant supporting arms extends radially from a central axis. Each arm has a plurality of pot receptacles which receive the plant seedling and liquid nutrients and water. The potting arms are rotated beneath grow lamps and pollinating arms. The frequency of feeding is increased as the plants grow. $CO_2$ enriched air may also be provided. Once the plants are ready to harvest, they are manually exchanged for new seedlings and packaged.

In addition to the exemplary aspects and embodiments described above, further aspects and embodiments will become apparent by reference to the drawings and by study of the following detailed descriptions.

BRIEF DESCRIPTION OF DRAWINGS

Exemplary embodiments are illustrated in referenced figures of the drawings. It is intended that the embodiments and figures disclosed herein are to be considered illustrative rather than restrictive.

DESCRIPTION

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

Figure 1:
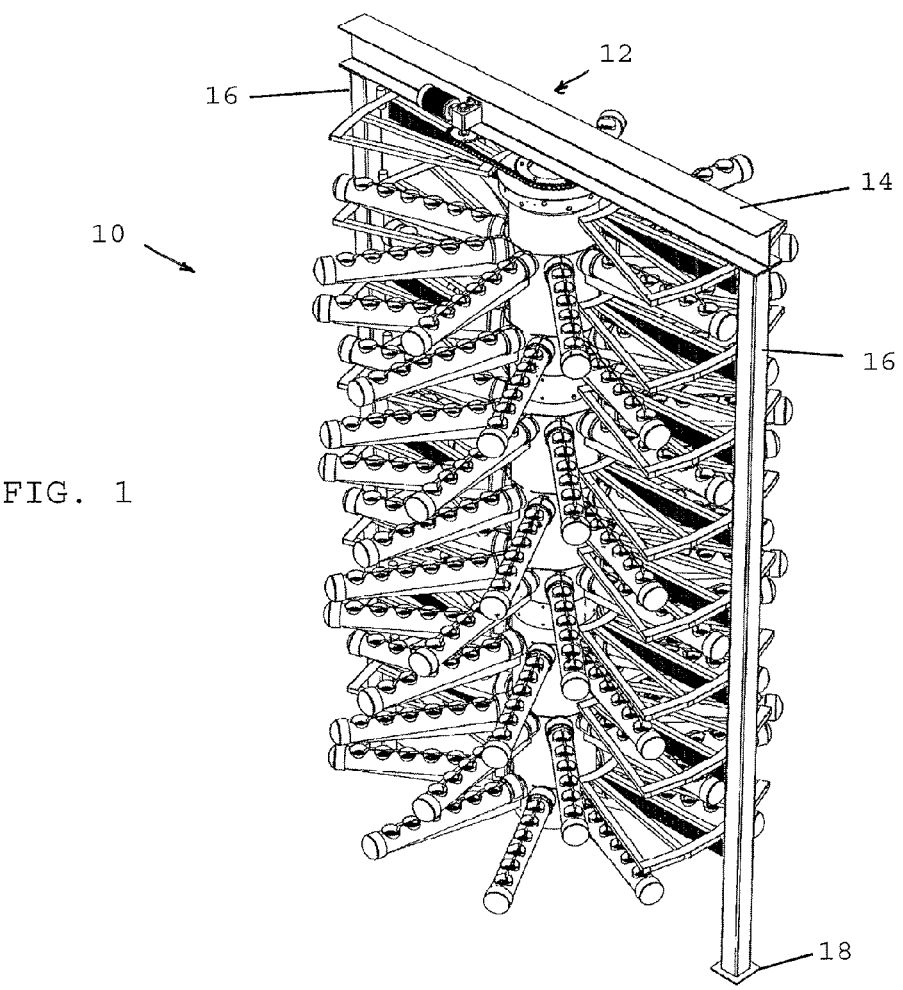
FIG. 1 is a perspective view of a growing unit for carrying out the method of the invention, with light bulbs removed for ease of illustration.

With reference to FIG. 1, a growing unit for automated vertical cultivation and harvesting of plants is designated generally as 10. It has a frame 12 including a horizontal beam 14 and vertical posts 16, the lower ends of which have flanges or feet 18 fixed to the floor of the growing facility.

Figure 3:
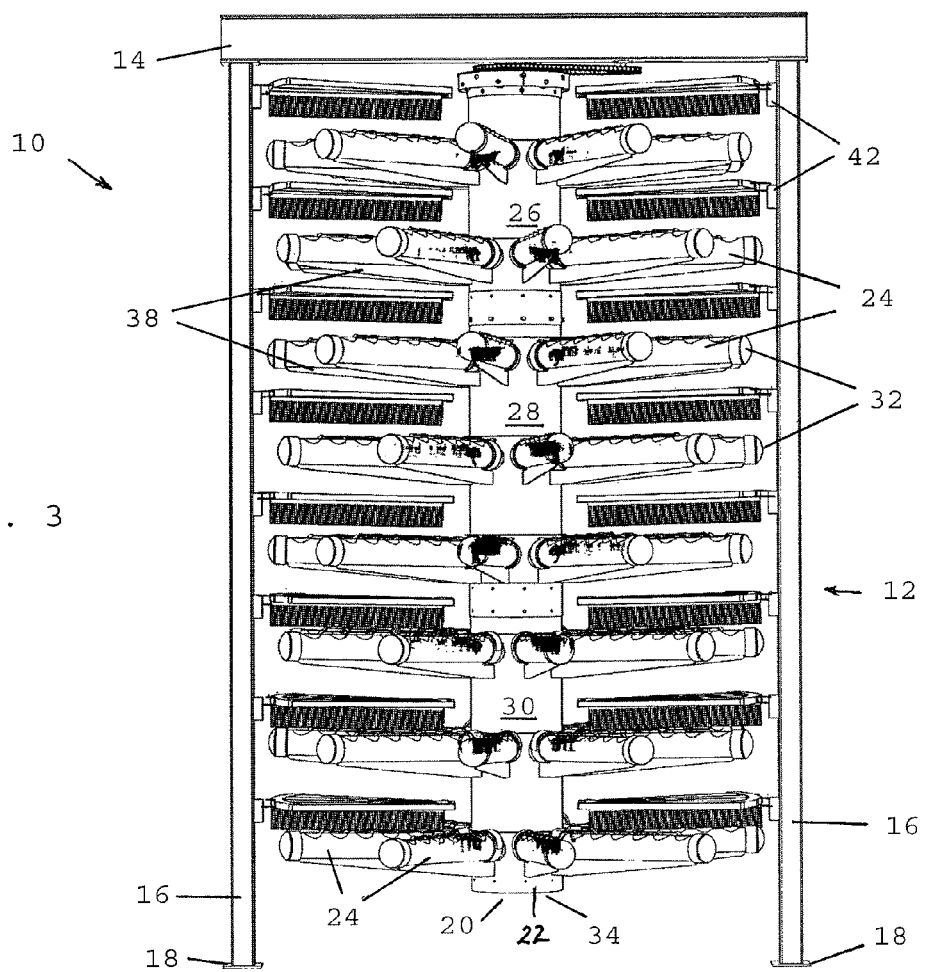
FIG. 3 is a front view of the growing unit shown in FIG. 1.
Figure 4:
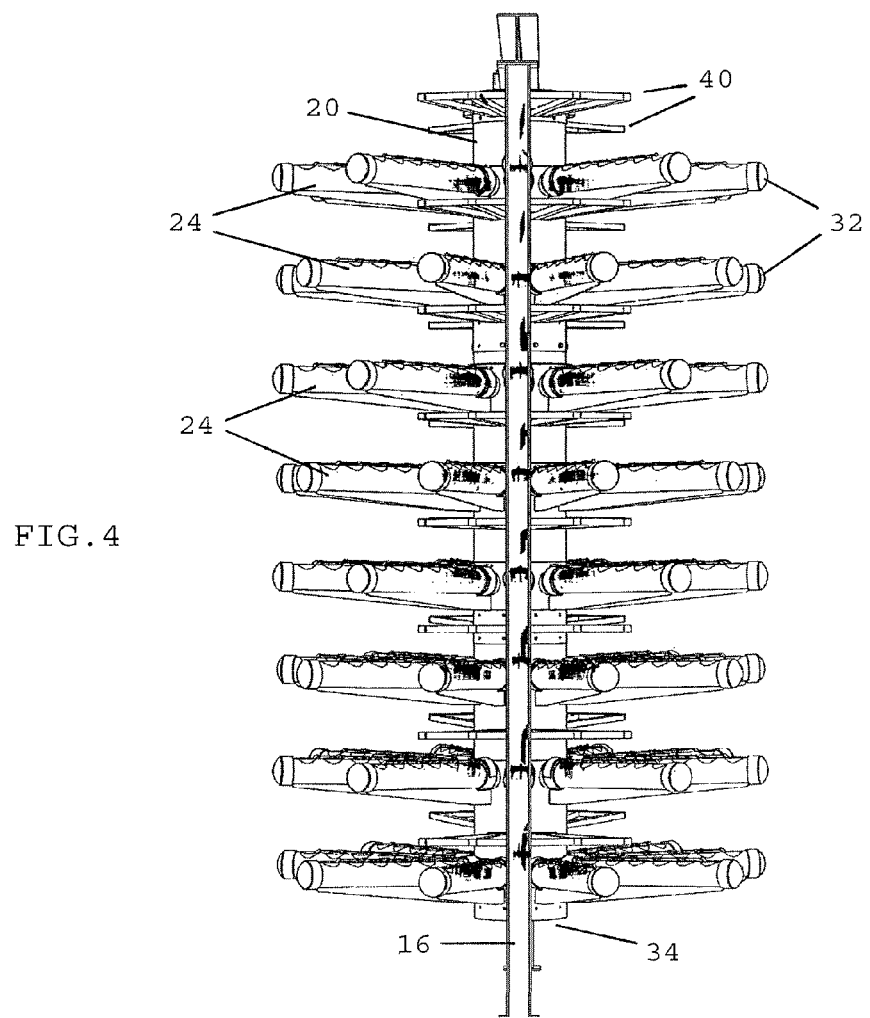
FIG. 4 is a side view of the growing unit shown in FIG. 1.
Figure 5:
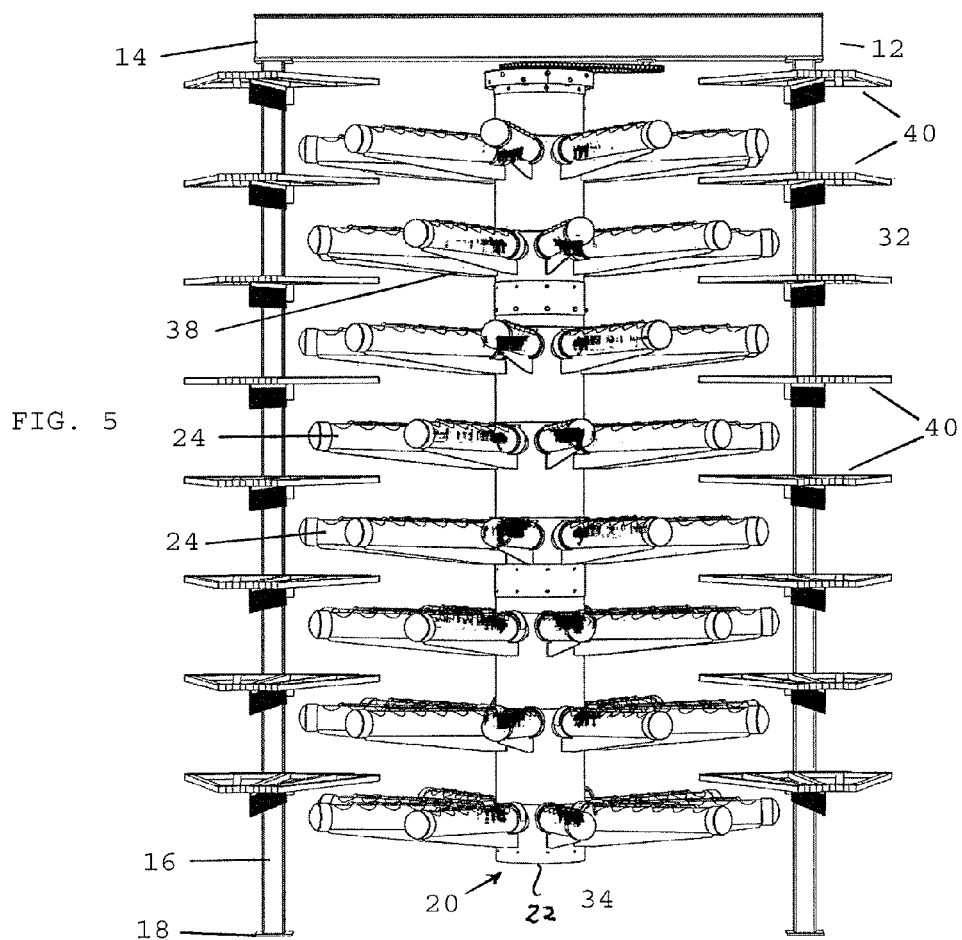
FIG. 5 is a front view of the growing unit shown in FIG. 1 with lighting fixtures swung out of operating position.

Rotating planter assembly 20 (FIG. 3) is suspended from beam 14. It includes a central drainage tube 22 from which a plurality of potting arms 24 are attached and extend radially. As shown in FIG. 3, central drainage tube 22 may comprise three tubing sections 26, 28, 30 secured together. Such sections may be PVC. In the embodiment shown there are 8 horizontal levels of potting arms 24 with 9 potting arms per level.

Potting arms 24 are each preferably PVC pipes, 6 inches in diameter and 2 feet or 4 feet long, closed at end 32 and attached to central drainage pipe 22 at the opposite end so that liquid flows from the interior of potting arms 24 into central drainage pipe 22 and out the bottom 34 of central drainage pipe 22 through a drainage outlet (not shown). Each potting arm 24 is provided with a plurality of pot receptacles 36, six per potting arm as shown, which are each sized to receive a seedling plant in a soil cylinder. Each pot receptacle is perforated to permit the flow of fluids from recess 36 into the interior of potting arm 24. Potting arms 24 are supported on brackets 38 and connect to central drainage pipe 22 by a fluid sealed pipe fitting.

Figure 2:
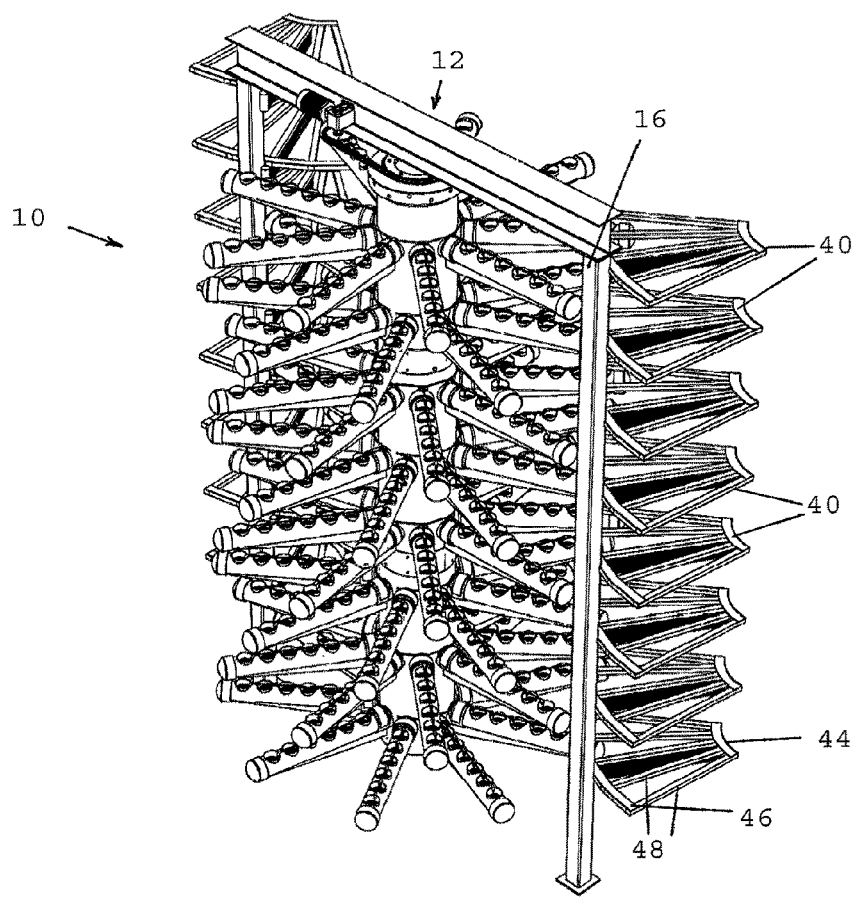
FIG. 2 is a perspective view of the growing unit shown in FIG. 1 with lighting fixtures swung out of operating position.

Horizontal light fixtures 40, shown in FIG. 2, are hingedly connected to vertical posts 16 at hinge 42 to permit them to swing into operational position shown in FIG. 1 and out of operational position as shown in FIG. 2. Fixtures 40 each have a frame formed of inner arc 44, outer arc 46 and radial frame members 48. Each fixture may carry ballasts and electrical connections for 10 T5 HO fluorescent bulbs, with electricity provided through connections 42 from vertical posts 16, controlled by a remotely controlled electrical switch. While fluorescent lamps are preferred, other growth promoting lights can be used, such as light emitting diodes (LEDs), high pressure sodium lamps, metal halide lamps or incandescent light bulbs. The electrical control switches may be programmed to provide a coordinated light cycle (photoperiod) for the plants at each growth stage and depending on the particular plant.

Figure 6:
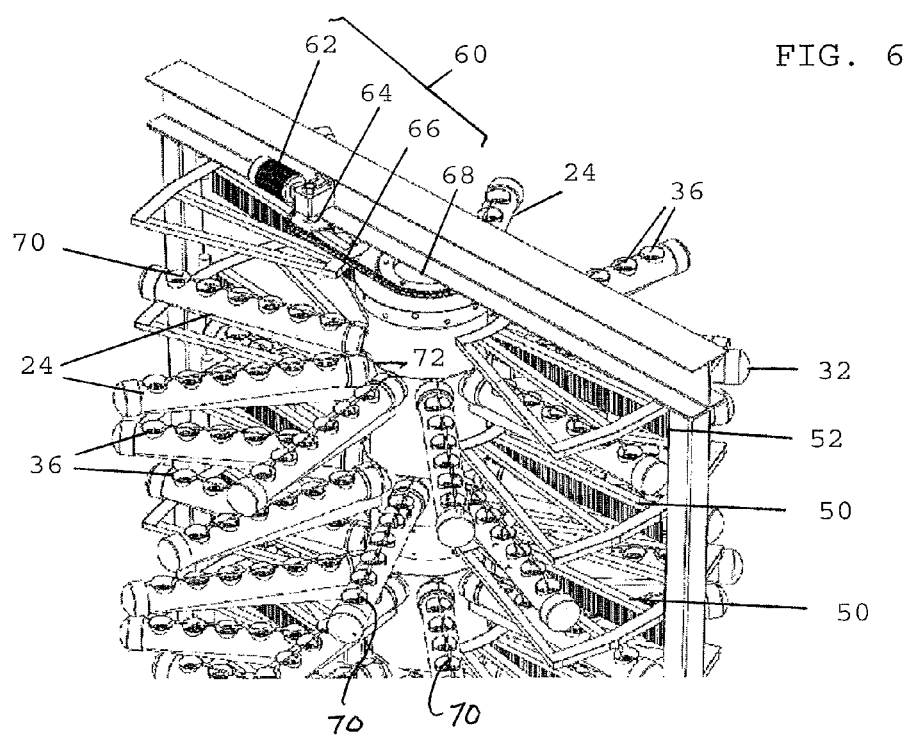
FIG. 6 is a detail of the perspective view shown in FIG. 1.

Attached to the central radial frame member 48 of each fixture 40 is a mechanical pollinator arm 50, formed of a suspended strip of micro-fibre strands 52 (see FIG. 6). Fixtures 40 can be individually raised or lowered on posts 16 by electrically powered activators, and activators may also provide power to swing each fixture 40 into and out of operating position as described above. Preferably the mechanical pollinator is kept at a height whereby the bottom 2 inches of the strands 52 brush over plants carried by the potting arms 24. Since the length of the strands 52 will typically be 4 or 5 inches, and the plants may reach a height of as much as 10 inches, there should be a clearance of about 14 inches between the fixture 40 and potting arms 24. As the plants grow, the fixtures 40 are elevated higher on post 16. An ultrasonic vibrator on or connected to each fixture 42 can also be provided to enhance the pollination activity of the mechanical pollinators 50. Also provided on the frame members 48 of each fixture 40 is an air emitting nozzle arm (not shown) which emits $CO^2$-enriched air onto the potting arms 24. Preferably compressed air is provided through an air line extending up vertical post 16 and through hinge element 42 and emits $CO^2$-enriched air onto the plants in potting arms 24.

With reference to FIG. 6, water and food is provided to plants in pot receptacles 36 by drip emitters 70 connected to and supplied by feed line 72. Drip emitters 70 are of the usual type used in greenhouses, hydroponics and other horticultural applications to provide a slow drip feed. Liquid feed lines 72 thus supply liquid nutrient solution to the pot receptacles 36 on each level through drip emitters 70. Liquid nutrient is delivered to the liquid feed lines 72 from feed tanks (not shown).

With reference to FIG. 6, drive system 60 has an electric motor 62, driving sprocket 64 which drives chain 66 which in turn drives sprocket 68 attached to central drainage pipe 22. Drive system 60 thus when activated rotates central drainage pipe 22 and attached potting arms 24 at a slow rate of rotation. Depending on the stage of growth and types of plants a typical rate of rotation is 4 rotations per hour. Rotation can be in either direction.

As an alternate embodiment (not shown), central discharge pipe 22 can be replaced with a circular array of chains, hanging downwardly from a circular drive plate attached to sprocket 68. Potting arms 24 are clipped onto brackets bolted onto the chains, one per chain. For example 16 arms can be attached per level, with 13 levels of arms and 4 pots per arm. Drainage may be carried through pipes on each chain as well as air lines and feed lines.

In operation seeded germination pucks are prepared in a separate location and each plant goes through a first germination stage prior to being placed in growing unit 10. After a sufficient germination period, and once the plants are ready to be transferred to the growing unit 10, a wheeled scissor lift is used to load the plants into the pot receptacles 36 on each level of potting arms 24. This is done manually on each scissor lift. One end of a conveyor is connected to the scissor lift and the plants are loaded on the other end of the conveyor. Scissor lifts are motorized to permit the scissor lifts to service a number of growing units 10. The plants remain on each growing unit 10 until they are ready to harvest. Once the plants are sufficiently mature, they are manually removed from each level onto a scissor lift and loaded onto a conveyor. Preferably new seedlings replace each harvested plant at the same time the plants are harvested. The plants can also be packaged at the time of harvesting on the scissor lift before being placed in the conveyor, and then stored in cold storage.

The growing facility may house a large number of growing units 10 and may also include the germination area, a packaging area, cold storage, cleaning area, seeding area and a feed tank storage area. In the example shown, each growing unit 10 handles 432 plants on a floor space of about 144 square feet for 4 foot potting arms 24.

Example—Strawberries

An example of application of the invention to the production of strawberries is described as follows. The preferred liquid nutrient solution mixes are:

i) a Bacterial Compost Tea mixed by, for each 20 L of filtered water adding 1.5 pounds (700 g) bacterial compost or vermicompost 3-4 tablespoons (45-60 ml) liquid black strap molasses 4 teaspoons (23 g) dry soluble kelp or 2 tablespoons of liquid kelp 3-4 teaspoons (15-20 ml) fish emulsion ii) as a fertilizer/nutrient solution, PURA VIDA™ GROW produced by Technaflora Plant Products of Mission BC, Canada. EDTA Iron is added at 20 ppm to the final solution. 1 gallon of compost tea is added for each 50 gallons of the feed solution with each new batch mixture.

In the germination stage, strawberry seeds are planted into Jiffy™ peat pucks (preferably Item #70000591), which are seed starting plugs. After about a week the plants are sprayed with the full strength compost tea solution at 5.8 pH. For the second week the media is soaked once per day with a 400 ppm fertilizer solution at 5.8 pH. After about 15 days the seedlings are transplanted into molded plastic pots 85 filled with 75% Botanicare™ Cocogro® Coir Fiber media to 25% perlite. Botanicare ZHO™ Root Inoculant is added according to the label directions and also added is 1 tbsp dolomite lime per gallon of media saturated in the same compost tea mix used in the seeding process. The pots are then placed in pot receptacles 36 on each level of growing unit 10. The temperature is maintained at 62 degrees F., the humidity is maintained at 68% and the light cycle is kept at 18 hours On, 6 hours Off. Rotation of the unit is 4 revolutions per hour. At days 15-30, the drip emitters are activated once a day with the fertilizer solution at 540 ppm at 5.8 pH. After about 30 days, the media is saturated at 1 EC (electrical conductivity) and plants are sprayed with the full strength compost tea solution brewed as above at 5.8 pH. From Days 30-45, the emitters are activated twice a day with the nutrient solution at 640 ppm at 5.8 pH. At day 45 the plants are harvested.

Thus using the invention, a continuous automated and controlled production of plants can be obtained. Different lighting, temperatures, humidity and nutrition can be programmed for the different growth stages of a crop and also for different crops. This can be done remotely by computer. The land space required to produce a crop is dramatically reduced and can be further reduced by increasing the height of the growing units 10. The entire process can be automated using robots to transfer the plants at different stages.

While the present apparatus and method are well-suited for strawberry production, many other types of plants can also be effectively produced using the present apparatus and method, such as lettuce, spinach, herbs, grape seedlings and tomato seedlings While a number of exemplary aspects and embodiments have been discussed above, those of skill in the art will recognize certain modifications, permutations, additions and sub-combinations thereof. It is therefore intended that the invention be interpreted to include all such modifications, permutations, additions and sub-combinations as are within their true spirit and scope.

What is claimed is:

1. Apparatus for continuous automated growing of plants, comprising:
    a) a frame comprising a horizontally-extending frame element supported by vertical frame elements;
    b) support means rotatably suspended vertically from said horizontally-extending frame element and rotatable about an axis;
    c) a plurality of vertically spaced, horizontal, generally co-planar arrays of hollow plant supporting arms extending radially from said support means wherein each plant supporting arm is provided with a plurality of pot receptacles which are each sized to receive a seedling plant in a soil cylinder;
    d) a plurality of light-supporting elements, each supported by said frame above a vertically spaced, horizontal, generally co-planar array of hollow plant supporting arms;
    e) a plurality of electric growth-promoting lights mounted on said light-fixture supporting elements;
    f) a plurality of liquid supply lines communicating with each pot receptacle and supplied by a liquid feed line to provide water and liquid nutrient to each said pot receptacle; and
    g) a motor for rotating said support means about said axis thereby rotating said plant supporting arms beneath grow lamps;
    wherein the interior of said potting arms communicates with the support means and each said pot receptacle is in liquid communication with the interior of the related plant supporting arm, whereby liquid flows from each said pot receptacle through the related plant supporting arm and into said support means.

2. The apparatus of claim 1 wherein said support means comprises a hollow pipe.

3. The apparatus of claim 1 further comprising a source of $CO_2$ enriched air for delivery to the vicinity of one or more of said pot receptacles.

4. The apparatus of claim 1 further comprising a plurality of pollinator arms attached to said light-supporting elements.

5. The apparatus of claim 4 wherein said pollinator arm comprises micro-fibre strands.

6. The apparatus of claim 4 further comprising an ultrasonic vibrator connected to the support for said pollinator arm to enhance the pollination activity.

7. The apparatus of claim 6 wherein said light-supporting elements can be individually raised, lowered, or pivoted by motors.

8. A method for continuous automated growing of plants, comprising:
    a) providing a plurality of vertically spaced, horizontal, generally co-planar arrays of hollow plant supporting arms extending radially from a rotatable support means wherein each plant supporting arm is provided with a plurality of pot receptacles which are each sized to receive a seedling plant in a soil cylinder and each provided with a source of liquid nutrients and water;
    b) placing a plurality of seedlings in soil cylinders in said plurality of pot receptacles;
    c) rotating said rotatable support to thereby rotate the plant supporting arms beneath grow lamps and pollinating arms;
    d) periodically providing water and liquid nutrients to each said pot receptacle;
    e) providing $CO_2$ enriched air to said pot receptacles;
    f) increasing the frequency of feeding as the plants grow over time;
    g) once the plants are ready to harvest, removing said plants.

9. The method of claim 8 wherein said pollinator arms comprise micro-fibre strands and the height of said pollinator arms is adjusted so that the ends of said microfibre brush the plants in said pot receptacles.

* * * * *